United States Patent [19]

Bondinell et al.

[11] 4,383,999

[45] May 17, 1983

[54] INHIBITION OF GABA UPTAKE BY N-SUBSTITUTED AZAHETEROCYCLIC CARBOXYLIC ACIDS AND THEIR ESTERS

[75] Inventors: William E. Bondinell, Cherry Hill, N.J.; John J. Lafferty, Levittown; Charles L. Zirkle, Berwyn, both of Pa.

[73] Assignee: Smithkline Beckman Corporation, Philadelphia, Pa.

[21] Appl. No.: 372,504

[22] Filed: Apr. 28, 1982

Related U.S. Application Data

[63] Continuation-in-part of Ser. No. 267,220, May 26, 1981, abandoned.

[51] Int. Cl.[3] .............. A61K 31/455; A61K 31/445; C07D 211/78; C07D 211/60
[52] U.S. Cl. .................................. 424/266; 424/267; 542/400; 542/429; 546/213; 546/221; 546/227; 546/239; 546/284; 546/322
[58] Field of Search ............. 542/429, 400; 546/213, 546/239, 284, 221, 227, 322; 424/266, 267

[56] References Cited

U.S. PATENT DOCUMENTS

3,575,990  4/1971  Hermans et al. ............ 546/216 X
4,024,264  5/1977  Bjork et al. ................. 546/221 X

FOREIGN PATENT DOCUMENTS

50-157376  12/1975  Japan ......................... 542/400

OTHER PUBLICATIONS

Sam, J., et al., *J. Am. Chem. Soc.*, 81:710–13 (1959).
Thayer, J., et al., *J. Am. Chem. Soc.*, 49:2862–9 (1928).
C. A. 59:13936f [Kempter, G., et al., *Z. Chem.*, 3(8), 305–7 (1963)].
Lee, D., et al., *J. Org. Chem.*, 39(7):893–902 (1974).
Derwent Abstract 34609F (1968).

*Primary Examiner*—Richard A. Schwartz
*Attorney, Agent, or Firm*—Richard D. Foggio; Alan D. Lourie

[57] ABSTRACT

N-Substituted azaheterocyclic carboxylic acids and their esters, useful as inhibitors of GABA uptake, are prepared by reacting an appropriate N-alkylating derivative with an ester of an N-unsubstituted azaheterocyclic carboxylic acid followed by hydrolysis of the ester.

21 Claims, No Drawings

INHIBITION OF GABA UPTAKE BY N-SUBSTITUTED AZAHETEROCYCLIC CARBOXYLIC ACIDS AND THEIR ESTERS

This application is a continuation-in-part of Ser. No. 267,220 filed May 26, 1981, now abandoned.

This invention relates to novel N-substituted azaheterocyclic carboxylic acids and their esters which are useful as inhibitors of neuronal and/or glial gamma-amino-butyric acid (GABA) uptake. GABA is a major inhibitory neurotransmitter of the central nervous system and is released into the synapse on nerve stimulation where it can modulate the activity of other neurons. Its actions are terminated primarily by uptake into the nerve terminal or into glial cells. Thus, inhibitors of neuronal and/or glial uptake of GABA would selectively enhance the activity of synaptically-released GABA by retarding the rate at which it is removed from the synapse. Enhancement of gabergic activity would be useful in the treatment of anxiety, epilepsy, muscular and movement disorders and mental and emotional disorders. Furthermore, these compounds may have analgesic and sedative effects as well.

The compounds of this invention are represented by the following general structural formulas:

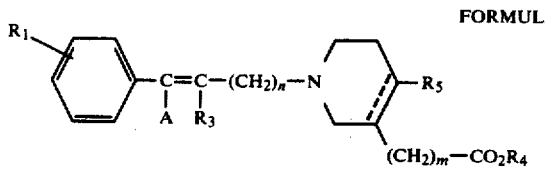

FORMULA I wherein:

A represents

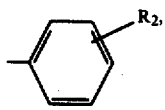

2-thienyl, 3-thienyl or cyclohexyl;

$R_1$ and $R_2$, which are the same or different, represent hydrogen, fluorine, chlorine, methyl or methoxy;

$R_3$ represents hydrogen or methyl;

n is a positive whole integer 2, 3 or 4;

m is a positive whole integer 0 or 1;

$R_4$ represents hydrogen or lower alkyl of from 1 to 4 carbon atoms;

the dotted line represents an optional double bond, when m is 0; and $R_5$ represents hydrogen or hydroxy, or when there is a double bond, hydrogen:

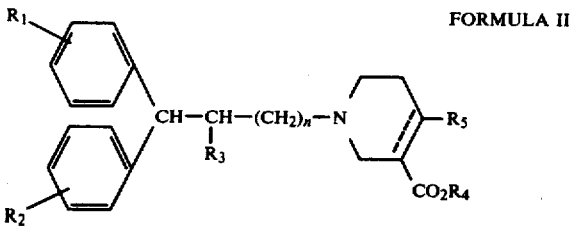

FORMULA II wherein:

$R_1$, $R_2$, $R_3$, $R_4$ and $R_5$, and the dotted line, are as defined above for formula I; and n is a positive whole integer 3 or 4;

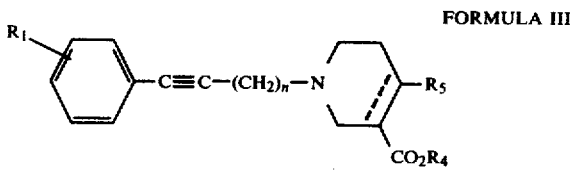

FORMULA III wherein: $R_1$, $R_4$, $R_5$, n and the dotted line are as defined above for formula I; and

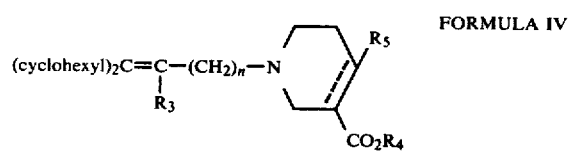

FORMULA IV wherein: $R_3$, $R_4$, $R_5$, n and the dotted line are as defined above for formula I.

Particular compounds of this invention represented by formula I above are when A is

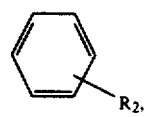

2-thienyl or cyclohexyl; $R_1$ and $R_2$ are hydrogen, fluorine, chlorine, methyl or methoxy, $R_3$ and $R_4$ are hydrogen, $R_5$ is hydrogen (with and without the double bond) or cis-hydroxy, m is 0, and n is 2; represented by formula II above are when $R_1$ and $R_2$ are hydrogen, fluorine, chlorine, methyl or methoxy, $R_3$ and $R_4$ are hydrogen and n is 3; and represented by formula III above are when $R_1$ is hydrogen, fluorine, chlorine, methyl or methoxy, $R_4$ is hydrogen and n is 2.

The pharmaceutically acceptable acid addition salts having the utility of the zwitterions of formulas I-IV above, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, theophylline acetic, benzenesulfonic, hydrochloric, hydrobromic, sulfuric, cyclohexylsulfamic, phosphoric and nitric acids.

Compounds of this invention may exist as geometric or optical isomers and it is intended to include herein all such isomers and mixtures thereof. The isomers may be separated by standard chromatographic or resolution techniques known to the art. Alternatively an optically active ester of an N-unsubstituted azaheterocyclic carboxylic acid may be employed as a starting material in the reactions described hereinbelow to provide the resolved optical isomers.

The compounds of formula I are conveniently prepared by reaction of an N-alkylating derivative with an ester of an N-unsubstituted azaheterocyclic carboxylic acid as shown in the following scheme:

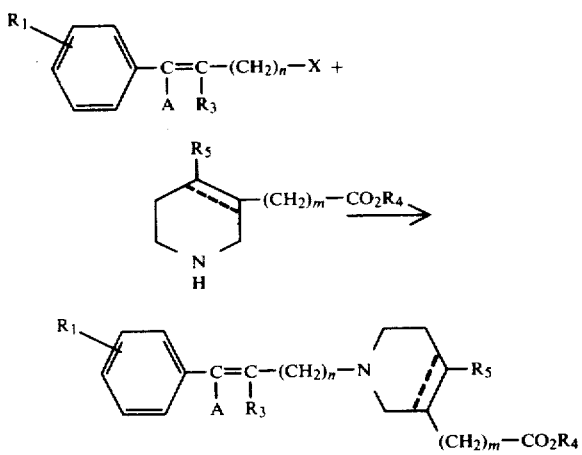

in which A, $R_1$, $R_2$, $R_3$, $R_5$, the dotted line, m and n are as defined above for formula I, X is a reactive leaving group preferably halo, for example bromo, or tosyl and $R_4$ is lower alkyl of from 1 to 4 carbon atoms. Thus, a disubstituted alkenyl halide is reacted with the ester, preferably in an inert organic solvent in which the reactants are soluble such as acetone or dimethylformamide, in the presence of an alkali metal carbonate such as potassium carbonate, at reflux temperature for from 8 to 48 hours. To obtain the free acid the ester product is hydrolyzed under acidic or basic conditions, such as refluxing in concentrated hydrochloric acid for from 12 to 18 hours or refluxing in a sodium hydroxide/methanol/water solution for from ½ to 4 hours.

The disubstituted alkenyl bromide starting material is obtained from an appropriately substituted phenyl ketone by reaction with a Grignard reagent followed by treatment with hydrogen bromide in acetic acid solution.

The compounds of formula II above are similarly prepared by reaction of an ester of an N-unsubstituted azaheterocyclic carboxylic acid with either a diphenyl alkyl moiety, substituted with a halo or other leaving group or, for example by catalytic hydrogenation, such as with palladium on charcoal, of the olefinic double bond in the side chain of an appropriate compound of formula I.

The compounds of formula III above are prepared by reaction of an ester of an N-unsubstituted azaheterocyclic carboxylic acid with a reactive ester of an appropriately substituted phenyl alkyne, substituted with a leaving group such as a tosyl group, similarly in the presence of an alkali metal carbonate such as potassium carbonate.

The compounds of formula IV above are similarly prepared by reaction of an ester of an N-unsubstituted azaheterocyclic carboxylic acid with a dicyclohexyl substituted alkenyl halide.

The free acids of formulas II, III and IV are similarly obtained by hydrolysis of the esters under acidic or basic conditions as described above.

The inhibition of GABA uptake produced by the compounds of this invention is measured by the ability of the active medicament to inhibit $^3$H-GABA uptake by a crude synaptosomal fraction ($P_2$) of the rat brain. In this test system, aliquots of the $P_2$ suspension are preincubated in a buffered physiological medium at 37° C. in the presence of test compound for 15 minutes. Uptake is initiated by the addition of $^3$H-GABA to a final concentration of 1 μM and terminated by filtration through a 0.45 μm Millipore filter. Incubation time is 3 minutes. A compound producing a 50% or greater inhibition of GABA uptake at concentrations of 10 μM is considered to show biosignificant activity. The $IC_{50}$ value is the concentration of a compound producing a 50% inhibition of GABA accumulation. For example, a particular compound of this invention, 1-(4,4-diphenyl-3-butenyl)-3-piperidinecarboxylic acid has an $IC_{50}$ of 0.2 μM. Similarly, 1-[(E/Z)-4-(4'-fluorophenyl)-4-phenyl-3-butenyl]-3-piperidinecarboxylic acid has an $IC_{50}$ of 0.283 μM; 1,2,5,6-tetrahydro-1-(4,4-diphenyl-3-butenyl)-3-pyridinecarboxylic acid has an $IC_{50}$ of 0.207 μM; 1-[(E/Z)-4-(4'-chlorophenyl)-4-phenyl-3-butenyl]-1,2,5,6,-tetrahydro-3-pyridinecarboxylic acid has an $IC_{50}$ of 0.358 μM; 1-[(E/Z)-4-(3'-chlorophenyl)-4-phenyl-3-butenyl]-1,2,5,6-tetrahydro-3-pyridinecarboxylic acid has an $IC_{50}$ of 0.280 μM; 1-(4,4-diphenyl-3-butenyl)-cis-4-hydroxy-3-piperidinecarboxylic acid has an $IC_{50}$ of 0.264 μM; 1-[4-phenyl-4-(2-thienyl)-3-butenyl]-3-piperidinecarboxylic acid has an $IC_{50}$ of 0.167 μM; and 1-[(Z)-4-cyclohexyl-4-phenyl-3-butenyl]-3-piperidinecarboxylic acid has an $IC_{50}$ of 0.179 μM.

The selectivity of the inhibition of GABA uptake by the compounds of this invention is demonstrated by the lack of significant inhibition of $^3$H-norepinephrine and/or $^3$H-serotonin uptake, the lack of activity in displacing $^3$H-muscimol or $^3$H-diazepam binding, or in noradrenergic, serotonergic, dopaminergic and cholinergic binding assays and the lack of significant reduction in the activity of glutamic acid decarboxylase (GAD) and GABA-transaminase (GABA-T), at concentrations which inhibit GABA uptake by 50%.

In vivo enhancement of GABA activity is demonstrated by potentiation of contralateral rotation in rats induced by unilateral injection of GABA into the pars reticulata of the substantia nigra. Compounds active in the in vitro test described above are tested by systemic administration for their ability to penetrate the central nervous system and potentiate the rotation induced by GABA. In this procedure 1-(4,4-diphenyl-3-butenyl)-3-piperidinecarboxylic acid was significantly active at doses from 2.5 to 40.0 mg/kg, I.P.

The compounds of this invention may be administered as pharmaceutical compositions in conventional dosage unit forms. These compositions which form a part of this invention are prepared by incorporating a compound of formulas I, II, III or IV, or a pharmaceutically acceptable acid addition salt thereof, in a nontoxic amount sufficient to produce inhibition of GABA uptake in an animal subject, with a nontoxic pharmaceutical carrier according to accepted procedures. Preferably the compositions will contain the active ingredient in an active but nontoxic amount selected from about 50 mg. to about 1000 mg. of active ingredient per dosage unit.

The pharmaceutical carrier employed may be, for example, either a solid or liquid, giving rise to a wide variety of pharmaceutical forms. If a solid pharmaceutical carrier is used, such as lactose, magnesium stearate, terra alba, sucrose, talc, stearic acid, gelatin, agar, pectin, acacia and the like, the composition can be tableted, used as a pharmaceutical powder, placed in a hard gelatin capsule or in the form of a troche or lozenge. The amount of solid carrier will vary widely but preferably will be from about 25 mg. to about 1 g. If a liquid pharmaceutical carrier is used, such as syrup, peanut oil, olive oil, sesame oil, propylene glycol, polyethylene glycol, water and the like, the composition will be in the form of a soft gelatin capsule, syrup, emulsion or a liquid suspension. Similarly the carrier or diluent may include a time delay material such as glyceryl monostearate or glyceryl distearate alone or with a wax.

The pharmaceutical preparations are made following the conventional techniques of the pharmaceutical chemist involving mixing, granulating and compressing when necessary, or variously mixing and dissolving the ingredients as appropriate to give the desired end product.

To produce inhibition of GABA uptake, a compound of formulas I, II, III or IV, or a pharmaceutically acceptable acid addition salt thereof, usually combined with a pharmaceutical carrier, is administered internally to an animal subject in need of such inhibition in a nontoxic amount sufficient to produce said inhibition. The route of administration may be oral or parenteral. Advantageously equal doses will be administered until a desired effect is obtained, for example 2 or 3 times a day, with the daily dosage regimen being selected from about 150 mg. to about 2000 mg. of active ingredient.

The following examples illustrate the preparation of specific compounds and pharmaceutical compositions of this invention and as such are not to be construed as limitations thereof. Those skilled in the art will appreciate that other modifications of the synthetic procedures described and the use of alternative starting materials may also be employed to prepare the compounds of formulas I, II, III or IV.

EXAMPLE 1

A mixture of 14.4 g. (0.05 mole) of 4,4-diphenyl-3-butenyl bromide, 0.05 mole of 3-piperidinecarboxylic acid ethyl ester, 0.1 mole of potassium carbonate and 0.2 g. of potassium iodide in 150 ml. of acetone was refluxed with stirring under nitrogen for 20 hours. The cooled reaction mixture was filtered, the filtrate made acidic with hydrogen chloride and the latter concentrated in vacuo to about 75 ml. This solution was treated with 30 ml. of ether and chilled overnight at 4° C.

The chilled mixture was decanted and the residue washed with ether. Crystallization of the solid from acetone gave 1-(4,4-diphenyl-3-butenyl)-3-piperidinecarboxylic acid ethyl ester, hydrochloride, m.p. 168°–169° C.

The ethyl ester, hydrochloride salt (12 g., 0.03 mole) was refluxed 17 hours in 5 N hydrochloric acid. The resulting solution (150 ml.) was concentrated in vacuo to 35–40 ml., treated with 4 ml. of concentrated hydrochloric acid and chilled for two hours. The mixture was decanted and the solid recrystallized from acetone to give 1-(4,4-diphenyl-3-butenyl)-3-piperidinecarboxylic acid hydrochloride, m.p. 188°–189° C.

EXAMPLE 2

A mixture of 5.0 g. (0.0282 mole) of 1,2,5,6-tetrahydro-3-pyridinecarboxylic acid methyl ester, hydrochloride, 8.08 g. (0.282 mole) of 4,4-diphenyl-3-butenyl bromide and 10 g. of crushed potassium carbonate was refluxed in 200 ml. of acetone for 15 hours. The reaction mixture was evaporated, extracted into ethyl acetate from water, dried, evaporated and chromatographed on silica (dry column) eluted with hexane/hexane:ethyl acetate to give 1,2,5,6-tetrahydro-1-(4,4-diphenyl-3-butenyl)-3-pyridinecarboxylic acid methyl ester hydrochloride.

The methyl ester (0.0195 mole) was dissolved in 100 ml. of methanol, treated with 100 ml. of 40% sodium hydroxide and refluxed for one hour. The reaction mixture was cooled, the methanol was evaporated and the aqueous layer was poured into 500 ml. of water. The solution was extracted with ether, the aqueous layer made acidic with 10% hydrochloric acid and extracted with ethyl acetate. The dried extract was evaporated and the solid slurried with ethyl acetate/ether to give 1,2,5,6-tetrahydro-1-(4,4-diphenyl-3-butenyl)-3-pyridinecarboxylic acid hydrochloride. Recrystallization from methanol-acetone-ether gave m.p. 178°–180° C.

EXAMPLE 3

To a suspension of 4.56 g. (0.188 mole) of magnesium turnings in 20 ml. of tetrahydrofuran under argon was added dropwise 25 g. (0.208 mole) of cyclopropyl bromide in 50 ml. of dried tetrahydrofuran and the mixture refluxed for two hours. The reaction mixture was cooled and 20.3 g. (0.094 mole) of 4-chlorobenzophenone in 50 ml. of dry tetrahydrofuran was added dropwise. After refluxing for one hour the mixture was cooled in an ice bath and 130 ml. of concentrated ammonium chloride solution was added carefully. The resulting solution was poured into water, extracted with ether and the ether extract was washed with water, dried and evaporated.

The residual oil was dissolved in 200 ml. of acetic acid and treated at 20° C. with 100 ml. of acetic acid and 50 ml. of 48% hydrobromic acid. The mixture was stirred, with cooling, for 30 minutes, poured into 1 l. of water and extracted with ether. The extract was washed with water, dried, evaporated and distilled in vacuo to give (E/Z)-4-(4'-chlorophenyl)-4-phenyl-3-butenyl bromide, b.p. 203°–213° C. (0.4–0.5 mm.).

A mixture of 5.0 g. (0.0282 mole) of 1,2,5,6-tetrahydro-3-pyridinecarboxylic acid methyl ester hydrochloride, 9.0 g. (0.0282 mole) of the butenyl bromide prepared above and 10 g. (0.0725 mole) of potassium carbonate in 200 ml. of acetone was refluxed for 15 hours. The reaction mixture was evaporated, partitioned between water and ethyl acetate and the organic layer was washed with water, dried, evaporated and chromatographed on silica (dry column) to give 1-[(E/Z)-4-(4'-chlorophenyl)-4-phenyl-3-butenyl]-1,2,5,6-tetrahydro-3-pyridinecarboxylic acid methyl ester.

The methyl ester (1.0 g., 0.0026 mole) was refluxed in 50 ml. of methanol and 20 ml. of 40% sodium hydroxide solution for one hour. The mixture was cooled, the methanol removed and the aqueous layer was acidified with 10% hydrochloric acid. The resulting solution was extracted with ethyl acetate and the dried extract evaporated to give a solid which on recrystallization from ethyl acetate afforded 1-[(E/Z)-4-(4'-chlorophenyl)-4-phenyl-3-butenyl]-1,2,5,6-tetrahydro-3-pyridinecarboxylic acid hydrochloride, m.p. 207°–209° C.

EXAMPLE 4

To a suspension of 6.4 g. (0.266 mole) of magnesium turnings in 50 ml. of tetrahydrofuran was added dropwise 51 g. (0.268 mole) of 3-bromochlorobenzene in 100 ml. of dried tetrahydrofuran and the mixture refluxed for one hour. The cooled reaction mixture was added to 27.4 g. (0.266 mole) of benzonitrile in 100 ml. of tetrahydrofuran and refluxed for one hour. The reaction mixture was poured carefully into 100 ml. of ice/water and 10 ml. of concentrated sulfuric acid and heated on a steam bath for 30 minutes. The solution was cooled, extracted with ether, washed with water and 5% sodium bicarbonate solution, dried, evaporated and chromatographed to give 3-chlorobenzophenone (recrystallized from methanol), m.p. 83° C.

A solution of 25 g. (0.208 mole) of cyclopropyl bromide in 50 ml. of dried tetrahydrofuran was added to 4.57 g. (0.188 mole) of magnesium turnings in 20 ml. of tetrahydrofuran and the mixture refluxed for one hour. To the cooled reaction mixture was added dropwise 21 g. (0.097 mole) of 3-chlorobenzophenone and the mixture refluxed for 30 minutes. The cooled reaction mixture was treated carefully with 100 ml. of concentrated ammonium chloride solution, poured into water, extracted with ether, washed with water, dried and evaporated. The residue was dissolved in 200 ml. of acetic acid at 20° C. and a solution of 100 ml. of acetic acid and 50 ml. of 48% hydrobromic acid was added in one portion. The resulting solution was stirred for 30 minutes in an ice bath, poured into 1 l. of water, extracted with ether, washed with water, dried, evaporated and distilled in vacuo to give (E/Z)-4-(3'-chlorophenyl)-4-phenyl-3-butenyl bromide, b.p. 184°–188° C. (0.4–0.5 mm.).

A mixture of 2.5 g. (0.0141 mole) of 1,2,5,6-tetrahydro-3-pyridinecarboxylic acid methyl ester, hydrochloride, 3.6 g. (0.011 mole) of the butenyl bromide prepared above and 5 g. (0.0363 mole) of potassium carbonate in 100 ml. of acetone was refluxed for 15 hours. The solvent was removed from the reaction mixture and the residue suspended in water. The mixture was extracted with ethyl acetate and the extract dried, evaporated and chromatographed on silica to give 1-[(E/Z)-4-(3'-chlorophenyl)-4-phenyl-3-butenyl]-1,2,5,6-tetrahydro-3-pyridinecarboxylic acid methyl ester.

The methyl ester (2 g., 0.0053 mole) in 50 ml. of methanol and 100 ml. of 40% sodium hydroxide solution was refluxed for 30 minutes. The reaction mixture was cooled, acidified with 10% hydrochloric acid and extracted with ethyl acetate. The dried extract was evaporated and the solid recrystallized from acetone/ethyl acetate to yield 1-[(E/Z)-4-(3'-chlorophenyl)-4-phenyl-3-butentyl]-1,2,5,6-tetrahydro-3-pyridinecarboxylic acid methyl ester hydrochloride, m.p. 206° C.

EXAMPLE 5

To a solution of cyclopropyl magnesium bromide (prepared from 18 g., 0.15 mole, of cyclopropyl bromide and 0.15 mole of magnesium turnings in 100 ml. of dry tetrahydrofuran) at 35° C. was added 20 g. (0.1 mole) of 4-fluorobenzophenone in 50 ml. of dry tetrahydrofuran and the mixture refluxed for four hours under nitrogen. To the cooled, stirred reaction mixture was added 50 ml. of saturated ammonium chloride solution followed by 150 ml. of water and 200 ml. of ether. The organic layer was washed with water, dried and evaporated. The residue was dissolved in 300 ml. of glacial acetic acid at 10° C. and a solution of 21 g. of hydrogen bromide in 150 ml. of glacial acetic acid was added. The mixture was stirred at about 15° C. for one hour, poured into 600 ml. of ice/water and extracted with ether. The extract was washed with water and then 5% sodium bicarbonate solution. The dried solution was evaporated in vacuo and the residue distilled to give (E/Z)-4-(4'-fluorophenyl)-4-phenyl-3-butenyl bromide, b.p. 145°–150° C. (0.6–0.8 mm.).

A mixture of 15.1 g. (0.05 mole) of the butenyl bromide prepared above, 7.9 g. (0.05 mole) of 3-piperidinecarboxylic acid ethyl ester, 13.8 g. (0.1 mole) of potassium carbonate and 0.2 g. of potassium iodide in 200 ml. of acetone was refluxed for 17 hours. The reaction mixture was filtered and the filtrate evaporated. The residue was taken up in 200 ml. of ether and 100 ml. of water. The ether layer was washed with water, dried and treated with dry hydrogen chloride to yield, after recrystallization from acetone, 1-[(E/Z)-4-(4'-fluorophenyl)-4-phenyl-3-butenyl]-3-piperidinecarboxylic acid ethyl ester hydrochloride, m.p. 107°–109° C.

The ethyl ester hydrochloride salt (6.2 g., 0.015 mole) was refluxed in 100 ml. of 5 N hydrochloric acid for 17 hours. The reaction mixture was evaporated in vacuo and the residue was recrystallized from acetone to give 1-[(E/Z)-4-(4'-fluorophenyl)-4-phenyl-3-butenyl]-3-piperidinecarboxylic acid hydrochloride, m.p. 179°–180° C.

EXAMPLE 6

Following the procedures of Example 5, a mixture of 6.5 g. of 4,4-bis-(4'-fluorophenyl)-3-butentyl bromide, 3.2 g. of 3-piperidinecarboxylic acid ethyl ester, 2.7 g. of potassium carbonate and 0.2 g. of potassium iodide in 100 ml. of acetone was refluxed for 24 hours. Similar workup of the reaction mixture gave 1-[4,4-bis-(4'-fluorophenyl)-3-butenyl]-3-piperidinecarboxylic acid ethyl ester, hydrochloride.

The ethyl ester hydrochloride salt (2.6 g.) was hydrolyzed in 75 ml. of 5 N hydrochloric acid to yield 1-[4,4-bis-(4'-fluorophenyl)-3-butenyl]-3-piperidinecarboxylic acid hydrochloride, m.p. 168°–169° C.

EXAMPLE 7

To a suspension of 3.9 g. (0.16 mole) of magnesium turnings in 300 ml. of dry ether was added dropwise 26.7 g. (0.16 mole) of 1-bromo-4-methoxybutane in 80 ml. of ether and the mixture refluxed for four hours. The reaction mixture was cooled and 14.6 g. (0.008 mole) of benzophenone in 100 ml. of dry ether was added dropwise. The mixture was stirred at ambient temperature for 18 hours, cautiously quenched with water and the ether layer separated. The aqueous layer was extracted with ether and the combined ether extract was dried and concentrated to give 1,1-diphenyl-5-methoxy-1-pentanol, m.p. 112°–115° C.

A mixture of the pentanol prepared as above (8.88 g., 0.0328 mole) in 132 ml. of glacial acetic acid and 66 ml. of distilled hydrobromic acid was stirred at ambient temperature for two hours and then refluxed for 90 minutes. The reaction mixture was cooled, diluted with water and extracted with ether. The ether extract was washed with 5% sodium carbonate solution, water, dried and concentrated to obtain an oil which is chromatographed on silica to yield 5,5-diphenyl-4-pentenyl bromide.

Following the procedures of Example 5, a mixture of 3.0 g. of the pentenyl bromide, 1.56 g. of 3-piperidinecarboxylic acid ethyl ester and 2.76 g. of potassium carbonate in 40 ml. of acetone was refluxed for 18 hours to yield upon similar workup 1-(5,5-diphenyl-4-pentenyl)-3-piperidinecarboxylic acid ethyl ester.

The ethyl ester (0.6 g.) was hydrolyzed in 20 ml. of 6 N hydrochloric acid to give 1-(5,5-diphenyl-4-pentenyl)-3-piperidinecarboxylic acid hydrochloride, m.p. 182°–184° C.

EXAMPLE 8

A solution of 2.0 g. (0.0053 mole) of 1-(5,5-diphenyl-4-pentenyl)-3-piperidinecarboxylic acid ethyl ester in 100 ml. of ethanol and 200 mg. of 5% palladium on charcoal in 20 ml. of ethanol were hydrogenated on the Parr apparatus for about 6 hours. The reaction mixture was filtered and the filtrate concentrated to an oil, 1-(5,5-diphenyl-pentyl)-3-piperidinecarboxylic acid ethyl ester. The ester (1.5 g.) was hydrolyzed in 100 ml. of 6 N hydrochloric acid to furnish 1-(5,5-diphenylpentyl)-3-piperidinecarboxylic acid hydrochloride, m.p. 199°–200.5° C.

EXAMPLE 9

A solution of 4-phenyl-3-butyn-1-ol (9.33 g., 0.0638 mole) in 78 ml. of pyridine was treated with 24.8 g. (0.128 mole) of tosyl chloride at 0° C. to give the corresponding tosylate. The latter (16.0 g., 0.533 mole) was refluxed with 0.0534 mole of 3-piperidinecarboxylic acid ethyl ester, 14.72 g. of potassium carbonate and 0.55 g. of potassium iodide in 267 ml. of acetone for 24 hours. Workup as described in Example 1 results in 1-(4-phenyl-3-butynyl)-3-piperidinecarboxylic acid ester hydrochloride, m.p. 173.5°–176.5° C.

The ester hydrochloride (4.05 g., 0.0126 mole) was hydrolyzed in 200 ml. of methanol and 25 ml. of 1.0 N sodium hydroxide (0.025 mole), treated with 13 ml. of 1.0 N hydrochloric acid, evaporated and the residue recrystallized from ethanol-ether to give 1-(4-phenyl-3-butynyl)-3-piperidinecarboxylic acid, m.p. 149.5°–151° C.

EXAMPLE 10

Sodium borohydride (7.4 g., 0.194 mole) in 150 ml. of ethanol was added dropwise to an ice-cold solution of 1-benzyl-4-oxo-3-piperidinecarboxylic acid methyl ester (24 g., 0.097 mole) in 160 ml. of ethanol under argon. After the addition was complete, the mixture was stirred in the cold for 10 minutes. The reaction mixture was quenched with water, the ethanol was removed in vacuo and the product was extracted into chloroform. The extract was dried and concentrated to give an oil which was chromatographed on silica gel eluted with 50:50 ethyl acetate/cyclohexane. The mixture of cis- and trans-1-benzyl-4-hydroxy-3-piperidinecarboxylic acid methyl ester was separated by preparative high pressure liquid chromatography, eluting with 2% methanol in chloroform containing 0.2% ammonium hydroxide.

The trans-alcohol (3.6 g., 0.0144 mole) was converted to its hydrochloride salt, dissolved in 150 ml. of methanol and 0.7 g. of 10% palladium on charcoal was added. The mixture was hydrogenated at 50 psi. at ambient temperature for 1.5 hours. The catalyst was filtered off and the filtrate was concentrated to give trans-4-hydroxy-3-piperidinecarboxylic acid methyl ester, hydrochloride, m.p. 149°–151° C.

The trans-alcohol hydrochloride (2.3 g., 0.0118 mole) and 4.24 g. (0.0148 mole) of 4,4-diphenyl-3-butenyl bromide were dissolved in 60 ml. of dimethylformamide and 2 g. of potassium carbonate and 0.3 g. of potassium iodide were added. The mixture was refluxed for 18 hours, cooled, poured into ice/5% sodium bicarbonate solution and extracted with hexane. The dried organic extract was concentrated and the residue chromatographed on silica to obtain 1-(4,4-diphenyl-3-butenyl)-trans-4-hydroxy-3-piperidinecarboxylic acid methyl ester. This ester (1.9 g., 0.0052 mole) was hydrolyzed in 50 ml. of hot 6 N hydrochloric acid to yield 1-(4,4-diphenyl-3-butenyl)-trans-4-hydroxy-3-piperidinecarboxylic acid hydrochloride, m.p. 167°–169° C.

Similarly, a mixture of 1.63 g. (0.00835 mole) of cis-4-hydroxy-3-piperidinecarboxylic acid methyl ester, hydrochloride, 3 g. (0.0104 mole) of 4,4-diphenyl-3-butenyl bromide, 1.5 g. of potassium carbonate and 0.2 g. of potassium iodide in 50 ml. of dimethylformamide was reacted as described above to give 1-(4,4-diphenyl-3-butenyl)-cis-4-hydroxy-3-piperidinecarboxylic acid methyl ester. This ester (1.4 g., 0.0038 mole) was hydrolyzed in 50 ml. of hot 6 N hydrochloric acid to obtain 1-(4,4-diphenyl-3-butenyl)-cis-4-hydroxy-3-piperidinecarboxylic acid hydrochloride, m.p. 174°–177° C.

EXAMPLE 11

Following the procedures of Example 5 the benzophenones:

3-methoxybenzophenone,
3-methylbenzophenone,
4-methylbenzophenone and
4,4'-bischlorobenzophenone were converted to the following compounds, respectively;

1-[(E/Z)-4-(3'-methoxyphenyl)-4-phenyl-3-butenyl]-3-piperidinecarboxylic acid hydrochloride, m.p. 159°–163° C., 1-[(E/Z)-4-(3'-methylphenyl)-4-phenyl-3-butenyl]-3-piperidinecarboxylic acid hydrochloride, m.p. 192°–193° C., 1-[(E/Z)-4-(4'-methylphenyl)-4-phenyl-3-butenyl]-3-piperidinecarboxylic acid hydrochloride, m.p. 97°–147° C. and 1-[4,4-bis(4'-chlorophenyl)-3-butenyl]-3-piperidinecarboxylic acid hydrochloride, m.p. 188°–191° C.

EXAMPLE 12

| Ingredients | Mg. per Capsule |
|---|---|
| 1-(4,4-diphenyl-3-butenyl)-3-piperidinecarboxylic acid (as an acid addition salt) | 50 (free base) |
| Magnesium stearate | 2 |
| Lactose | 200 |

The above ingredients are mixed, passed through a #40 mesh screen, remixed and filled into #2 capsules.

EXAMPLE 13

| Ingredients | Mg. per Tablet |
|---|---|
| 1,2,5,6-tetrahydro-1-(4,4-diphenyl-3-butenyl)-3-pyridinecarboxylic acid (as an acid addition salt) | 100 |
| Calcium sulfate, dihydrate | 75 |
| Sucrose | 25 |
| Starch | 15 |
| Talc | 5 |
| Stearic acid | 3 |

The sucrose, calcium sulfate and active ingredient are thoroughly mixed and granulated with hot 10% gelatin solution. The wetted mass is passed through a #6 mesh screen directly onto drying trays. The granules are dried at 50° C. and passed through a #20 mesh screen, mixed with the starch, talc and stearic acid, and compressed into tablets.

The capsules or tablets prepared as in Examples 12 and 13 are administered internally to an animal subject requring inhibition of GABA uptake within the dose ranges set forth hereinabove. Similarly other compounds of formulas I, II, III or IV can be formulated in the same manner to give pharmaceutical compositions useful in producing inhibition of GABA uptake.

EXAMPLE 14

Following the procedures of Example 1 but employing d-(+)-3-piperidinecarboxylic acid ethyl ester and l-(−)-3-piperidinecarboxylic acid ethyl ester (each obtained from the corresponding tartrate salt) yielded the analogous products d-(+)-1-(4,4-diphenyl-3-butenyl)-3-piperidinecarboxylic acid hydrochloride, m.p. 209°–211° C., $[\alpha]_{589}^{25} = +1.006°$, $[\alpha]_{578}^{25} = +0.79°$, $[\alpha]_{546}^{25} = +0.85°$ (all solutions 5% in methanol) and l-(−)-1-(4,4-diphenyl-3-butenyl)-3-piperidinecarboxylic acid hydrochloride, m.p. 209°–211° C., $[\alpha]_{589}^{25} = -1.16°$, $[\alpha]_{578}^{25} = -1.12°$, $[\alpha]_{546}^{25} = -1.00°$ (all solutions 5% in methanol).

EXAMPLE 15

To a solution of 29.6 g. (0.2 mole) of cyclopropyl magnesium bromide in 70 ml. of dry tetrahydrofuran was added over 20 minutes 18.8 g. (0.1 mole) of cyclohexyl phenyl ketone in 70 ml. of dry tetrahydrofuran under nitrogen atmosphere and at 30° C. The resulting mixture was refluxed for two hours, chilled in an ice bath and treated with 180 ml. of saturated aqueous ammonium chloride solution and 150 ml. of ether. The dried ether layer was evaporated in vacuo and the residue (18.4 g.) was dissolved in 250 ml. of glacial acetic acid. This solution was treated with 200 ml. of 20% hydrogen bromide in glacial acetic acid at 10°–15° C. and the mixture was stirred for one hour at this temperature. The reaction mixture was poured into 1 l. of water and extracted with ether. The extract was washed with 5% sodium carbonate solution, dried and evaporated in vacuo to give (E/Z)-4-cyclohexyl-4-phenyl-3-butenyl bromide, b.p. 155°–160° C. (0.6–0.9 mm.).

A mixture of 14.8 g. (0.05 mole) of the butenyl bromide prepared above, 7.8 g., (0.05 mole) of 3-piperidinecarboxylic acid ethyl ester, 13.8 g. (0.1 mole) of potassium carbonate and 0.2 g. of potassium iodide in 175 ml. of acetone was refluxed under nitrogen for 20 hours. The reaction mixture was filtered and the filtrate was treated with gaseous hydrogen chloride to pH 2. Addition of 100 ml. of ether precipitated 1-[(E/Z)-4-cyclohexyl-4-phenyl-3-butenyl]-3-piperidinecarboxylic acid ethyl ester hydrochloride, m.p. 97°–107° C.

The E/Z mixture of esters prepared above was recrystallized from acetone and allowed to stand at room temperature for 72 hours. The precipitated E isomer was recrystallized from acetone to melt at 100°–112° C. The Z isomer was isolated by concentration of the acetone filtrate and cooling to 5° C., m.p. 124°–126° C.

The separated E and Z ethyl ester isomers were refluxed for 17 hours in 5 N hydrochloric acid. Concentration of the reaction mixtures, followed by recrystallization of the solids from acetone yielded 1-[(E)-4-cyclohexyl-4-phenyl-3-butenyl]-3-piperidinecarboxylic acid hydrochloride, m.p. 155°–156° C. and 1-[(Z)-4-cyclohexyl-4-phenyl-3-butenyl]-3-piperidinecarboxylic acid hydrochloride, m.p. 187°–188° C.

EXAMPLE 16

Following the procedures of Example 15, 9.7 g. (0.05 mole) of dicyclohexyl ketone and 14.4 g. (0.1 mole) of cyclopropyl magnesium bromide in dry tetrahydrofuran were reacted and the resulting carbinol dissolved in glacial acetic acid was treated with hydrogen bromide to give 4,4-dicyclohexyl-3-butenyl bromide, b.p. 168°–171° C. (0.1 mm.).

A mixture of the above butenyl bromide (9.7 g., 0.016 mole), 2.6 g. (0.016 mole) of 3-piperidinecarboxylic acid ethyl ester, 4.4 g. of potassium carbonate and 0.1 g. of potassium iodide in 100 ml. of acetone was refluxed for 17 hours. Workup of the reaction mixture and similar treatment with hydrogen chloride yielded 1-(4,4-dicyclohexyl-3-butenyl)-3-piperidinecarboxylic acid ethyl ester hydrochloride, m.p. 143°–145° C. The latter (3.9 g., 0.01 mole) was refluxed in 100 ml. of 5 N hydrochloric acid for 18 hours to yield upon evaporation 1-(4,4-dicyclohexyl-3-butenyl)-3-piperidinecarboxylic acid hydrochloride, m.p. 183°–184° C.

EXAMPLE 17

Following the procedures of Example 2, a mixture of 7.9 g. (0.05 mole) of 3-piperidineacetic acid methyl ester (obtained from the acid by treatment with absolute methanol/sulfuric acid), 14.4 g. (0.05 mole) of 4,4-diphenyl-3-butenyl bromide and 13.82 g. (0.1 mole) of potassium carbonate in 200 ml. of acetone was refluxed for 20 hours, filtered and the filtrate concentrated to give 1-(4,4-diphenyl-3-butenyl)-3-piperidineacetic acid methyl ester. The latter (5.0 g., 0.0137 mole) was dissolved in 30 ml. of methanol, 60 ml. of 20% sodium hydroxide solution were added and the mixture was refluxed for one hour. The methanol was evaporated from the reaction mixture and the aqueous solution was extracted with ether. The separated oily layer was dissolved in water, extracted with ether and acidified with concentrated hydrochloric acid to pH 1. The solution was concentrated to dryness and the semi-solid dissolved in alcohol, filtered and the filtrate concentrated. This residue was dissolved in water, basified with ammonium hydroxide solution to pH 9 and lyophilized. The residual material was dissolved in chloroform and filtered. The filtrate was dissolved in methanol and a methanolic solution of maleic acid was added. Ether was added and after standing there was obtained 1-(4,4-diphenyl-3-butenyl)-3-piperidineacetic acid maleate, m.p. 178°–180° C.

EXAMPLE 18

Following the procedures of Examples 15 and 17, 9.4 g. (0.050 mole) of phenyl 2-thienyl ketone and cyclopropyl magnesium bromide (obtained from 2.43 g. of magnesium and 13.3 g. of cyclopropyl bromide) in tetrahydrofuran were refluxed for two hours to give the corresponding cyclopropyl carbinol which is treated with 48% hydrobromic acid in glacial acetic acid to furnish (E/Z)-4-phenyl-4-(2-thienyl)-3-butenyl bromide, b.p. 86°–96° C. (0.015–0.025 mm.). The latter (6.52 g.) with a mixture of 3-piperidinecarboxylic acid ethyl ester (22.2 mmole), potassium carbonate and potassium iodide in 110 ml. of acetone was refluxed for 48 hours. The reaction mixture was filtered and the filtrate evaporated to leave a solid which was purified as the hydrochloride salt by recrystallization from methanol/ether to give 1-[(E/Z)-4-phenyl-4-(2-thienyl)-3-butenyl]-3-piperidinecarboxylic acid ethyl ester, hydrochloride, m.p. 148°–150° C. The ester hydrochloride (3.62 g., 8.42 mmole) dissolved in methanol was hydrolyzed with 19.2 ml. of 0.932 N sodium hydroxide solution. The methanol was removed, hydrochloric acid was added and the resulting mixture evaporated to dryness. Inorganic salt was removed by filtration of an ethanolic suspension, the filtrate was evaporated and the residue taken up in methanol. Treatment of the methanolic solution with hexamic acid gave the 1-[(E/Z)-4-phenyl-4-(2-thienyl)-3-butenyl]-3-piperidinecarboxylic acid hexamate, m.p. 105.5° C. (foam).

We claim:

1. A compound represented by one of the formulas:

FORMULA I

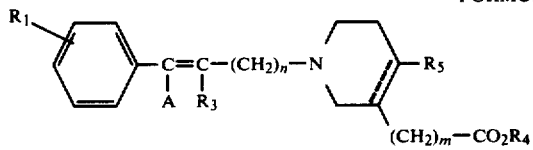

wherein:

A is

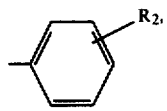

2-thienyl, 3-thienyl or cyclohexyl;

$R_1$ and $R_2$, which are the same or different, are hydrogen, fluorine, chlorine, methyl or methoxy;

$R_3$ is hydrogen or methyl;

n is a positive whole integer 2, 3 or 4;

m is a positive whole integer 0 or 1;

$R_4$ is hydrogen or lower alkyl of from 1 to 4 carbon atoms;

the dotted line represents an optional double bond, when m is 0; and $R_5$ is hydrogen or hydroxy, or when there is a double bond, hydrogen;

FORMULA II

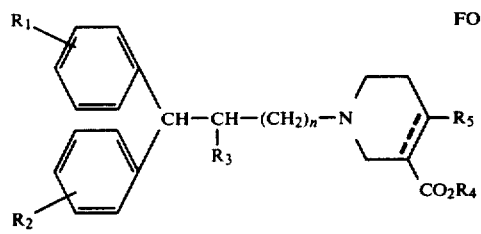

wherein: $R_1$, $R_2$, $R_3$, $R_4$ and $R_5$, and the dotted line, are as defined above for formula I, and n is a positive whole integer 3 or 4;

FORMULA III

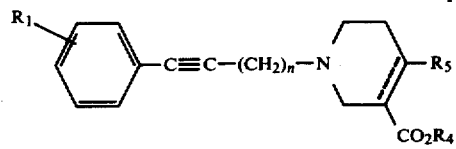

wherein: $R_1$, $R_4$, $R_5$, n and the dotted line are as defined above for formula I;

FORMULA IV

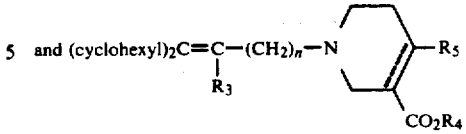

and $(cyclohexyl)_2C=C-(CH_2)_n-N$ wherein: $R_3$, $R_4$, $R_5$, n and the dotted line are as defined above for formula I;

or a pharmaceutically acceptable acid addition salt thereof.

2. A compound according to claim 1 having formula I in which A is

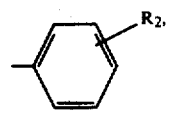

2-thienyl or cyclohexyl, $R_1$ and $R_2$ are hydrogen, fluorine, chlorine, methyl or methoxy, $R_3$ and $R_4$ are hydrogen, $R_5$ is hydrogen, with and without the double bond, or hydroxy, m is 0, and n is 2.

3. A compound according to claim 2 which is 1-(4,4-diphenyl-3-butenyl)-3-piperidinecarboxylic acid or a pharmaceutically acceptable acid addition salt thereof.

4. The compound according to claim 3 in the form of its hydrochloride salt.

5. A compound according to claim 2 which is 1-[(E/Z)-4-(4'-fluorophenyl)-4-phenyl-3-butenyl]-3-piperidinecarboxylic acid or a pharmaceutically acceptable acid addition salt thereof.

6. A compound according to claim 2 which is 1,2,5,6-tetrahydro-1-(4,4-diphenyl-3-butenyl)-3-pyridinecarboxylic acid or a pharmaceutically acceptable acid addition salt thereof.

7. The compound according to claim 6 in the form of its hydrochloride salt.

8. A compound according to claim 2 which is 1-[(E/Z)-4-(4'-chlorophenyl)-4-phenyl-3-butenyl]-1,2,5,6-tetrahydro-3-pyridinecarboxylic acid or a pharmaceutically acceptable acid addition salt thereof.

9. A compound according to claim 2 which is 1-[(E/Z)-4-(3'-chlorophenyl)-4-phenyl-3-butenyl]-1,2,5,6-tetrahydro-3-pyridinecarboxylic acid or a pharmaceutically acceptable acid addition salt thereof.

10. A compound according to claim 2 which is 1-(4,4-diphenyl-3-butenyl)-cis-4-hydroxy-3-piperidinecarboxylic acid or a pharmaceutically acceptable acid addition salt thereof.

11. A compound according to claim 2 which is 1-[(E/Z)-4-(3'-methoxyphenyl)-4-phenyl-3-butenyl]-3-piperidinecarboxylic acid or a pharmaceutically acceptable acid addition salt thereof.

12. A compound according to claim 2 which is 1-[(E/Z)-4-(3'-methylphenyl)-4-phenyl-3-butenyl]-3-piperidinecarboxylic acid or a pharmaceutically acceptable acid addition salt thereof.

13. A compound according to claim 2 which is 1-[(E/Z)-4-(4'-methylphenyl)-4-phenyl-3-butenyl]-3-piperidinecarboxylic acid or a pharmaceutically acceptable acid addition salt thereof.

14. A compound according to claim 2 which is 1-[4,4-bis(4'-chlorophenyl)-3-butenyl]-3-piperidinecarboxylic acid or a pharmaceutically acceptable acid addition salt thereof.

15. A compound according to claim 2 which is 1-[(Z)-4-cyclohexyl-4-phenyl-3-butenyl]-3-piperidinecarboxylic acid or a pharmaceutically acceptable acid addition salt thereof.

16. A compound according to claim 2 which is 1-[(E/Z)-4-phenyl-4-(2-thienyl)-3-butenyl]-3-piperidinecarboxylic acid or a pharmaceutically acceptable acid addition salt thereof.

17. A compound according to claim 1 having formula I which is 1-(4,4-diphenyl-3-butenyl)-3-piperidineacetic acid or a pharmaceutically acceptable acid addition salt thereof.

18. A compound according to claim 1 having formula II in which $R_1$ and $R_2$ are hydrogen, fluorine, chlorine, methyl or methoxy, $R_3$ and $R_4$ are hydrogen and n is 3.

19. A compound according to claim 1 having formula III in which $R_1$ is hydrogen, fluorine, chlorine, methyl or methoxy, $R_4$ is hydrogen and n is 2.

20. A compound according to claim 1 having formula IV which is 1-(4,4-dicyclohexyl-3-butenyl)-3-piperidinecarboxylic acid or a pharmaceutically acceptable acid addition salt thereof.

21. A pharmaceutical composition for inhibiting GABA uptake in dosage unit form comprising a pharmaceutical carrier and an amount sufficient to produce said inhibition of a compound of claim 1, 3, 4, 5, 6, 7, 8, 9, 10, 11, 12, 13, 14, 15, 16, 17 or 20, or a pharmaceutically acceptable acid addition salt thereof.

* * * * *